(12) United States Patent
Orbay et al.

(10) Patent No.: US 7,686,808 B2
(45) Date of Patent: Mar. 30, 2010

(54) FRACTURE FIXATION DEVICE AND IMPLANTATION JIG THEREFOR

(75) Inventors: Jorge L. Orbay, Miami, FL (US); Javier E. Castaneda, Miami, FL (US); Edward Mebarak, Miami Beach, FL (US)

(73) Assignee: Depuy Products, Inc., Warsaw, IN (US)

( * ) Notice: Subject to any disclaimer, the term of this patent is extended or adjusted under 35 U.S.C. 154(b) by 350 days.

(21) Appl. No.: 11/342,114

(22) Filed: Jan. 27, 2006

(65) Prior Publication Data

US 2007/0191855 A1    Aug. 16, 2007

(51) Int. Cl.
*A61F 5/00* (2006.01)
*A61B 17/56* (2006.01)

(52) U.S. Cl. ..................................... 606/86 R; 606/62
(58) Field of Classification Search .............. 606/62–68, 606/87, 89, 86 R, 96, 99, 86 B
See application file for complete search history.

(56) References Cited

U.S. PATENT DOCUMENTS

| | | | |
|---|---|---|---|
| 4,465,065 | A | 8/1984 | Gotfried |
| 5,366,457 | A | 11/1994 | McGuire et al. |
| 5,458,654 | A | 10/1995 | Tepic |
| 5,658,283 | A | 8/1997 | Huebner |
| 5,853,415 | A | 12/1998 | Bertin et al. |
| 5,928,234 | A | 7/1999 | Manspeizer |
| 6,514,253 | B1 | 2/2003 | Yao |
| 6,527,775 | B1 | 3/2003 | Warburton |
| 6,579,293 | B1 | 6/2003 | Chandran |
| 6,692,496 | B1 | 2/2004 | Wardlaw |
| 6,706,046 | B2 | 3/2004 | Orbay et al. |
| 6,746,453 | B2 | 6/2004 | Delogé et al. |

(Continued)

FOREIGN PATENT DOCUMENTS

EP    737444 A1 * 10/1996

(Continued)

OTHER PUBLICATIONS

Article: "The Hand Sourcebook" (Instruments for Surgeons) by K. Medic; dated 2002; 5 pgs.

(Continued)

*Primary Examiner*—Eduardo C Robert
*Assistant Examiner*—Ellen C. Hammond
(74) *Attorney, Agent, or Firm*—Gordon & Jacobson, PC (57) ABSTRACT

A fracture fixation device includes a plate portion and an intramedullary nail portion which is offset relative to the plate portion by a neck portion. The plate portion includes longitudinally displaced peg holes which orient pegs along an imaginary surface parallel to subchondral bone of an articular surface. The upper surface of the plate portion includes a dimple to reference a jig. The nail portion includes threaded screw holes oriented normal to an endosteal surface, and a smaller K-wire alignment hole parallel to the screw holes. The jig has a first portion which references with the dimple and a second portion in alignment over the screw holes of the nail portion. The back of the first portion of the jig is curved upward to facilitate maneuvering of the jig. The first and second portions of the jig includes K-wire guide holes which direct K-wires relative to holes in the device.

14 Claims, 5 Drawing Sheets

U.S. PATENT DOCUMENTS

| | | |
|---|---|---|
| 6,926,720 B2 | 8/2005 | Castañeda |
| 2003/0055428 A1 | 3/2003 | Swanson |
| 2003/0083661 A1* | 5/2003 | Orbay et al. .................. 606/69 |
| 2003/0216742 A1 | 11/2003 | Wetzler et al. |
| 2007/0173839 A1* | 7/2007 | Running et al. ............... 606/69 |
| 2007/0173843 A1* | 7/2007 | Matityahu .................... 606/69 |

FOREIGN PATENT DOCUMENTS

WO     WO 2005053548 A1 *   6/2005

OTHER PUBLICATIONS

Article SCS/D "Distal Radius Plate System"; Avanta Orthopaedics 1997; 6 pgs.

\* cited by examiner

FRACTURE FIXATION DEVICE AND IMPLANTATION JIG THEREFOR

RELATED APPLICATION

The application is related to U.S. Pat. No. 6,926,720, which is hereby incorporated by reference herein in its entirety.

BACKGROUND OF THE INVENTION

1. Field of the Invention

This invention relates broadly to surgical devices. More particularly, this invention relates to surgical devices and tools for implanting fracture fixation devices.

2. State of the Art

Severe long bone fractures are often treated with plating. In plating, a relatively large incision is made at the location of the fracture, musculature and tendons are displaced from the bone to expose the bone surface, and a bone plate is fixedly attached to one or more pieces of the fractured bone in a manner which, ideally, supports and stabilizes the fracture for healing. Due to the relatively invasive nature of the procedure required to implant the plate, plating is generally reserved for fractures which cannot be treated with a less invasive method of immobilization.

Less complicated fractures are often treated with casting or wires. However, such conservative treatment may not provide the stabilization and support necessary for desirable recovery. Yet, the operative procedure of plating is often too invasive for the relative non-severity of the fracture. Moreover, conventional plating can result in tendon irritation and skin necrosis, and may require extensive periosteal stripping in order to apply the plate on the bone surface. As such, many of the less displaced fractures, and particularly metaphyseal fractures (fractures at the end of the long bones), remain under-treated.

By way of example, a Colles' fracture, which results from compressive forces being placed on the distal radius bone, and which causes backward displacement of the distal fragment and radial deviation of the hand at the wrist, is treated with a dorsal plate when there is a significant degree of displacement. However, a less-displaced Colles' fracture is commonly under-treated due to the hesitancy of physicians to prescribe operative and invasive treatment. If not properly treated, such a fracture results in permanent wrist deformity. It is therefore important to align the fracture and fixate the bones relative to each other so that proper healing may occur.

More recently, relatively minimally invasive fixation devices have become available for treatment of wrist fractures. For example, U.S. Pat. No. 6,379,359 to Dahners teaches an intrafocal fixation device including an intracellular portion and a plate portion which seats at the metaphysis. However, devices like that described in Dahners are not likely to obtain acceptance by surgeons or be effective without addressing several critical issues. First, the subchondral bone must be properly supported. Second, the support must be properly aligned on the bone. Third, the support for the subchondral bone needs to be applied in a manner which is not counter to the minimally invasive design of the implant. Fourth, the implant should not necessitate undue removal of bone, which may further weaken the fracture location. It is therefore necessary to provide to the surgeon with a fracture fixation implant and a jig facilitating the implant thereof.

SUMMARY OF THE INVENTION

It is therefore an object of the invention to provide a fixation device and a jig for assistance in implantation of the fixation device relative to a fractured bone.

It is another object of the invention to provide a fixation device designed to treat metaphyseal fractures.

It is a further object of the invention to provide a jig assembly which provides proper alignment between longitudinally displaced holes drilled in bone and corresponding openings in an intracellular portion of the fixation device such that fasteners can be inserted through the holes and openings.

It is an additional object of the invention to provide a jig assembly which facilitates drilling of axially aligned holes through peg holes in a plate of a fixation device and through metaphyseal bone.

In accord with these objects, which will be discussed in detail below, a fracture fixation device and a jig therefor are provided.

A fracture fixation device according to the invention a supra-metaphyseal plate portion and an intracellular nail portion which is horizontally and vertically offset relative to the plate portion by a neck portion. The plate portion includes longitudinally displaced fixed angle holes, each of which is adapted to orient a peg (or locking screw, collectively referred to as 'peg') in a different angular orientation such that pegs therethrough generally corresponds to the articular surface of the subchondral bone. The nail portion includes threaded screw holes oriented normal to an endosteal surface, and a smaller K-wire alignment hole parallel to the screw holes.

An implantation jig for the fixation device has a first portion with a concave surface seatable on the plate portion of the fixation device, and a relatively elevated second portion in alignment over the screw holes of the intracellular nail portion of the fixation device.

The first portion includes openings in alignment with the fixed angle holes. A cannulated locking drill guide locks the jig relative to the implant and is used to guide a drill in alignment with one of the fixed angle holes. The back of the first portion of the jig is curved upward to facilitate maneuvering the nail portion of the fixation device within the intrafocal space and to allow the first portion to rest on the diaphyseal-side of the fracture during the implantation process. The first portion of the jig includes two K-wire guide holes which extend on either side of the front end of plate portion when the jig is coupled to the plate portion. The K-wire guide holes are designed to closely hold an appropriately sized K-wire and direct it at a fixed angle parallel to the endmost screw hole of the plate portion. Two such guide holes are provided, as the endmost holes for left and right fixation devices (for left and right hands) each have opposite respective angles, and the jig may be used with each of the left and right devices. For a particular application, the K-wire guide hole located on the side of the operative limb (left or right hand) is used. The respective K-wire guide hole defines an axis which is substantially parallel to and closely spaced to the axis of the endmost screw hole, thus anticipating the path of a peg through the endmost screw hole. In use, prior to drilling any holes into bone for the pegs for the screw holes, a K-wire is drilled into bone through the appropriate K-wire guide hole and its placement within the bone is viewed under fluoroscopy to ensure its placement, and the subsequent placement of the peg through the endmost screw hole, relative to the articular surface of the subchondral bone is appropriate.

The second portion of the jig includes longitudinally displaced holes or slots for drill guides. The second portion also includes a K-wire guide hole configured to direct a K-wire at a fixed angle into the K-wire alignment hole of the nail portion of the fixation device. Similar to above, prior to drilling any holes into the diaphysis for the screws for the nail portion, a K-wire is drilled through the K-wire guide hole in the second portion and its placement can be viewed under fluoroscopy to ensure its placement relative to the diaphysis is appropriate.

Additional objects and advantages of the invention will become apparent to those skilled in the art upon reference to the detailed description taken in conjunction with the provided figures.

DETAILED DESCRIPTION OF THE PREFERRED EMBODIMENTS

Turning now to FIGS. 1 through 4, a fracture fixation device 10 according to the invention includes a supra-metaphyseal plate portion 12 and an intracellular nail portion 14 which is horizontally and vertically offset relative to the plate portion by a neck portion 16. The plate portion 12 has a narrow profile and is slightly rounded about its upper surface 20. The plate portion 12 includes four longitudinally displaced fixed angle holes 22, 24, 26, 28, each preferably threaded, and each of which is adapted to lock a fastener, such as a smooth or threaded shaft peg 30, in a different orientation from the others (i.e., the axes are oblique relative to each other). When viewed from the plate end of the device, the pegs 30 are laterally displaced defining an imaginary surface (generally transverse to the longitudinal axis A of the plate portion) which generally corresponds to (i.e., extends parallel to) the articular surface of the subchondral bone. The plate portion 12 includes a dimple 32 for referencing an implantation jig, as described below. The nail portion 14 includes three threaded screw holes 34, 36, 38 oriented normal to a preferably flattened endosteal surface 40, and a smaller K-wire alignment hole 42 parallel to the screw holes and sized to closely receive a K-wire at a fixed angle. The tail end 44 of the nail portion 14 is provided with a portion 46 having downward and then upward curve which facilitates maneuvering the tail end of the nail portion through the intrafocal space and into the medullary canal.

Figure 1:
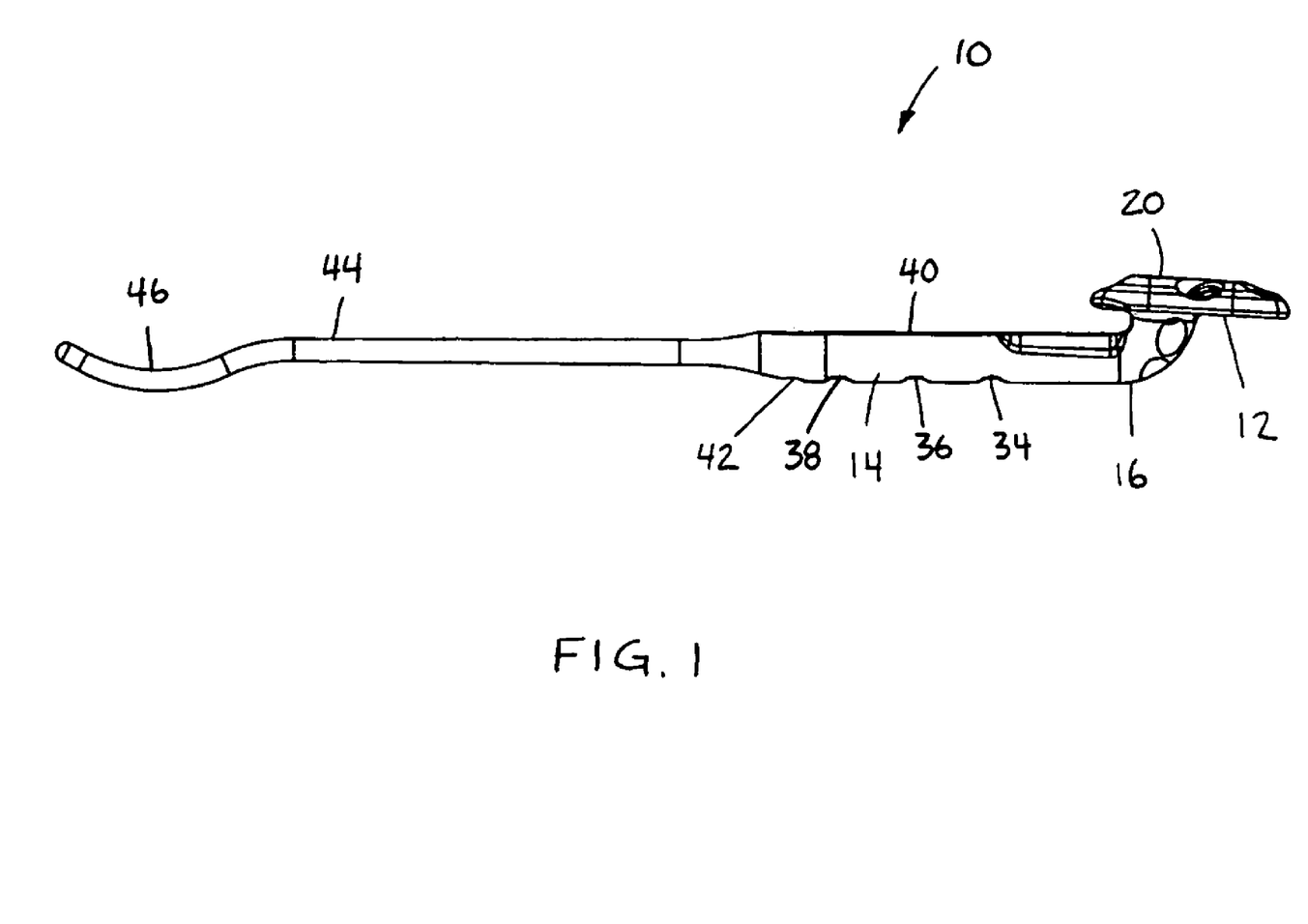
FIG. 1 is a side elevation of a fixation device according to the invention.
Figure 2:
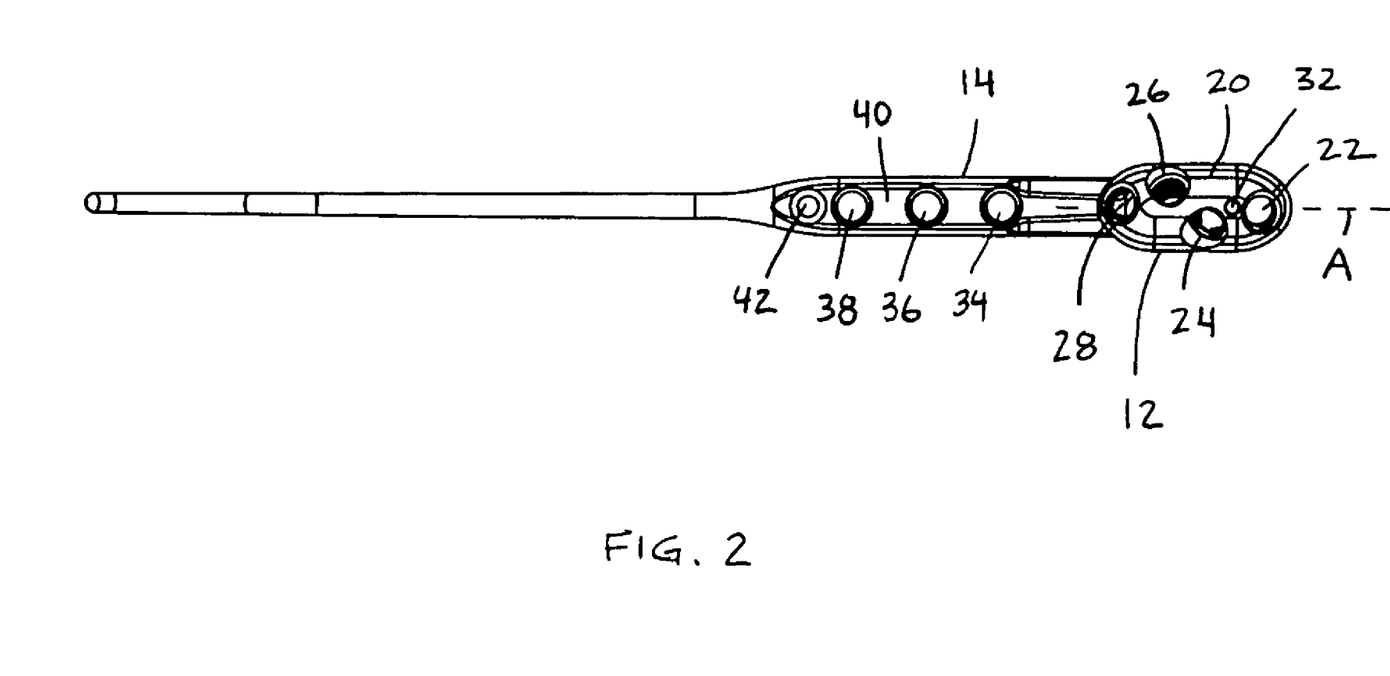
FIG. 2 is a plan view of a fixation device according to the invention.
Figure 3:
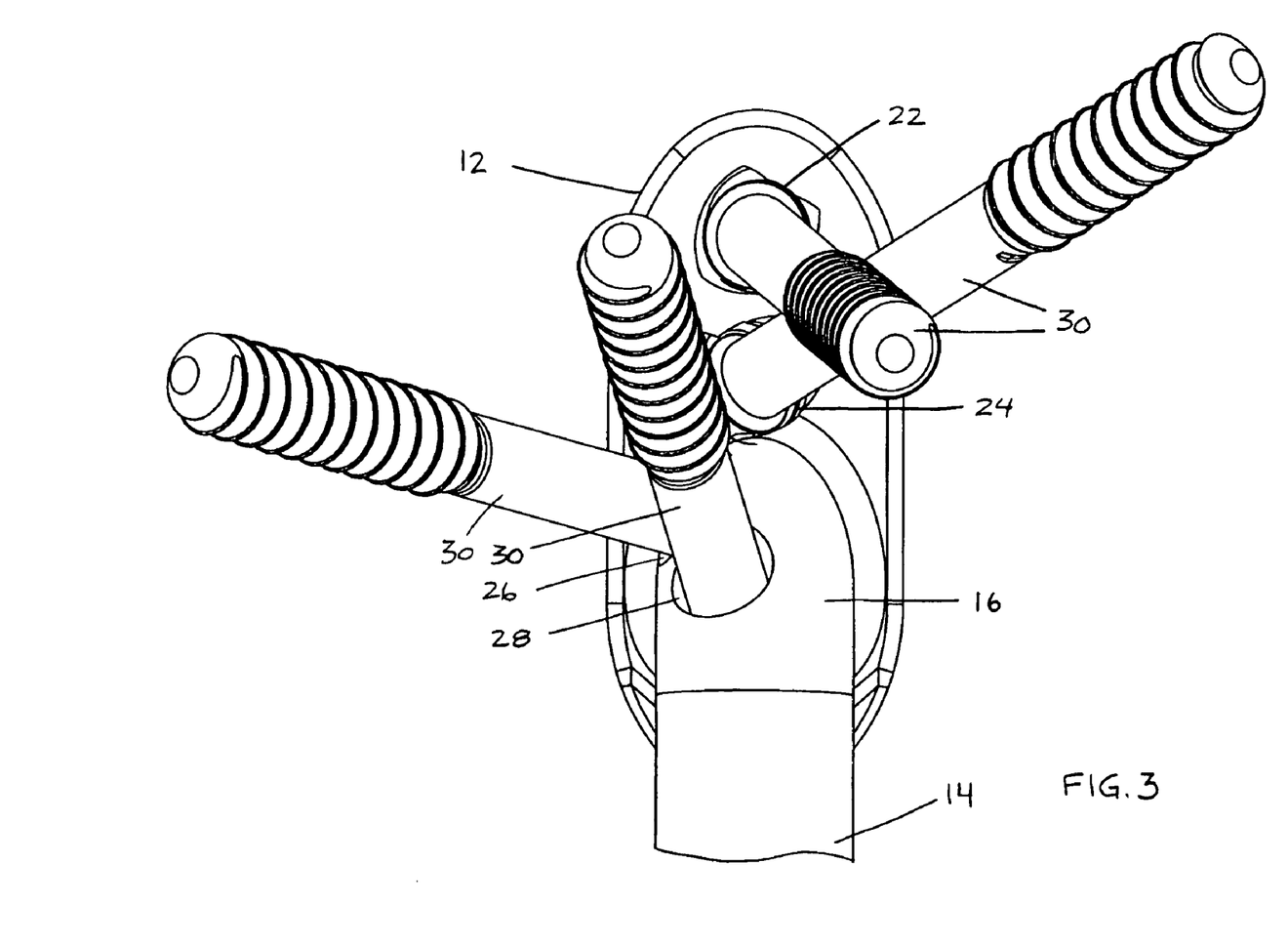
FIG. 3 is a bottom view of the plate-portion end of the fixation device of the invention.
Figure 4:
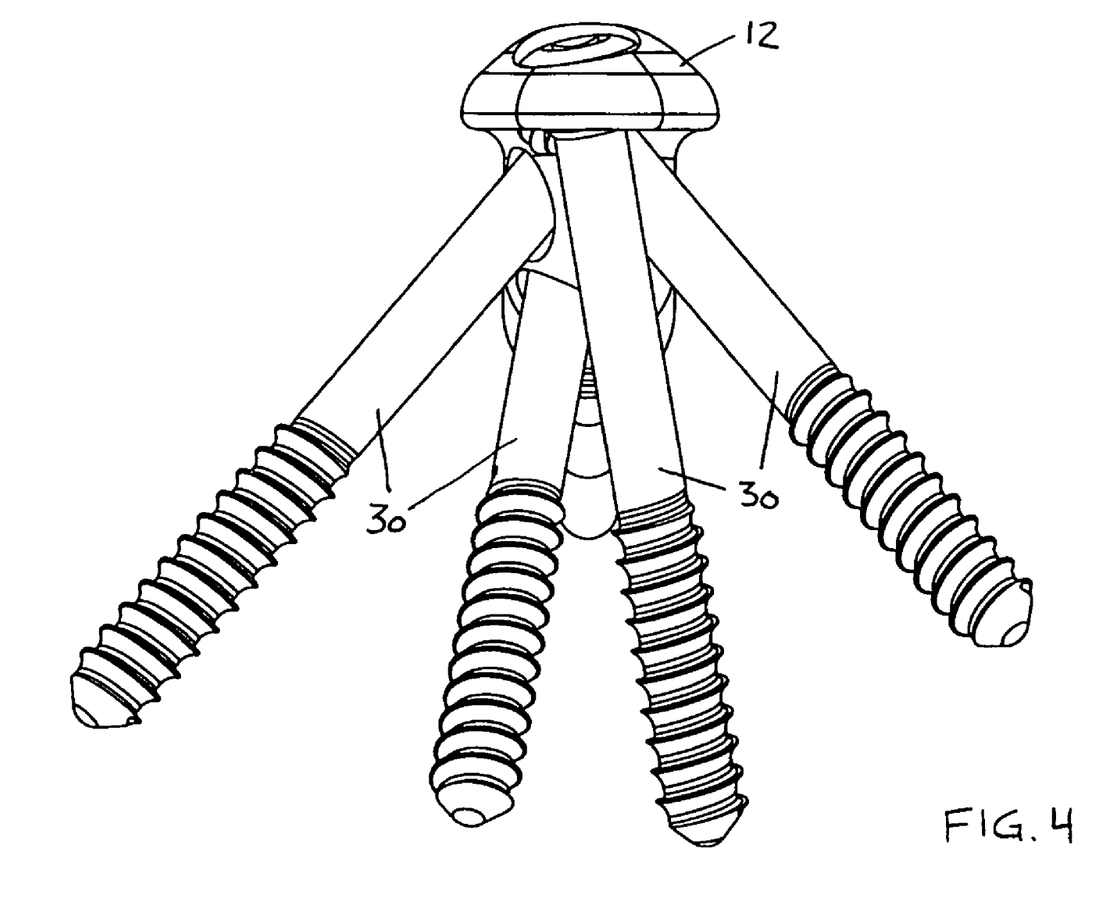
FIG. 4 is a plate-portion end view of the fixation device of the invention.
Figure 5:
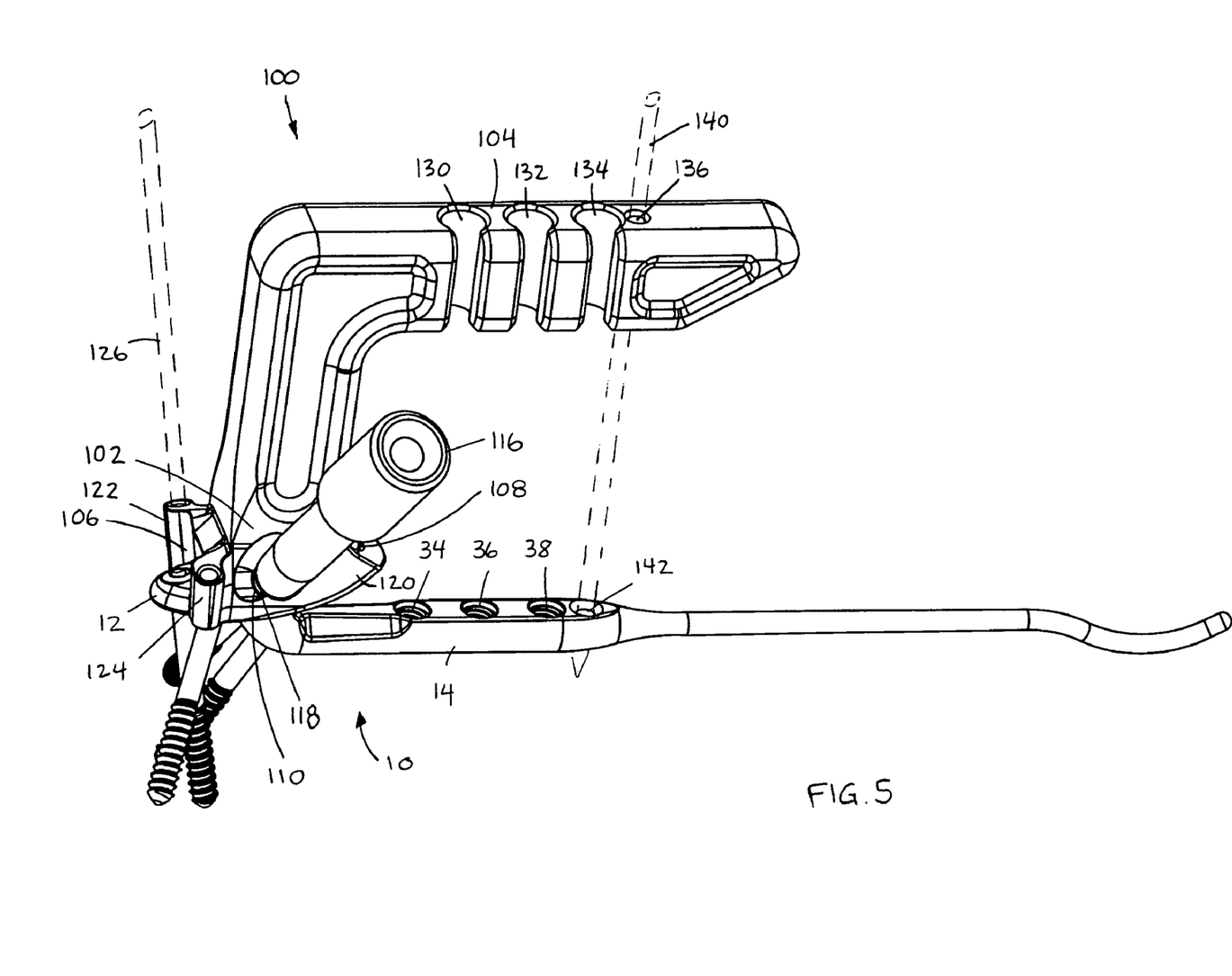
FIG. 5 is a perspective view of an implantation jig according to the invention coupled to the fixation device of the invention.

With the fixation device 10 in mind, turning now to FIG. 5, an implantation jig 100 for the fixation device has a first portion 102 seatable on the plate portion 12 of the fixation device, and a relatively elevated second portion 104 in alignment over the screw holes 34, 36, 38 of the intracellular nail portion 14 of the fixation device 10.

The first portion 102 includes a lower nub (not shown) which seats in the dimple 32 (FIG. 2) on the plate portion 12 of the fixation device. In addition, the first portion includes access openings 106 (at the front), 110 (at the left side, and at right the side, not shown), 108 (at the rear) in axial alignment with the fixed angle screw holes 22, 24, 26, 28. Such openings are preferably initially positioned over drill guide tips (not shown) which are inserted in all of the fixed angle holes of the plate portion but the hole beneath access opening 110. The drill guide tips which functions as miniature drill guides, are described in detail in co-owned U.S. Ser. No. 11/011,917, filed Dec. 14, 2004, which is hereby incorporated by reference herein in its entirety. As another option, the drill guides tips are not necessitated, and individual drill guides can be inserted into the fixed angle holes just prior to drilling holes into bone in alignment with the holes.

In accord with one aspect of the invention, a cannulated locking drill guide 116 having a threaded end 118 is provided through opening 110 and thread into hole 26 in the plate portion 12, such that a portion of the guide 116 applies a force against said jig 100. The locking drill guide 116 in conjunction with the engagement of the nub within the dimple 32 immobilizes the jig 100 relative to the fixation device 10 so that the two are fixed relative to each other.

In accord with another aspect of the invention, the back 120 of the first portion 102 of the jig 100 is curved upward to facilitate maneuvering the nail portion 14 of the fixation device within the intrafocal space and to allow the first portion to rest on the diaphyseal-side of the fracture (e.g., the proximal cortex of the distal radius) during the implantation process.

The plate portion 12 of the fixation device 10 is too narrow to support the inclusion of K-wire guide holes. Thus, in accord with a further aspect of the invention, the first portion 102 of the jig 100 includes two K-wire guide holes 122, 124 which extend on either side of the front of the plate portion when the jig 100 is fixed relative to the fixation deice 10 to guide a K-wire offset relative to the plate portion. The K-wire guide holes 122, 124 are designed to closely hold an appropriately sized K-wire 126 and direct it at a fixed angle parallel to the endmost screw hole 22 (e.g., distalmost where the fixation device is used at the distal radius). Two such guide holes are provided, as the endmost holes for left and right fixation devices (for left and right hands) each have opposite respective angles, and the same jig may be used with each of the left and right devices. For a particular application, the K-wire guide hole located opposite the side on which the locking drill guide is positioned is used. That is, as shown in FIG. 5, with the locking drill guide on the left side of the plate, the right side K-wire guide hole 122 is used. The respective K-wire guide hole 122 defines an axis which is laterally offset, substantially parallel to, and closely spaced to the axis of the endmost screw hole 22 (preferably within approximately 5 mm), thus anticipating the path of a peg through the endmost screw hole 22. In use, prior to drilling any holes into bone for the pegs 30 for the screw holes, a K-wire 126 is drilled into bone through the appropriate K-wire guide hole 122 and its placement within the bone is viewed under fluoroscopy to ensure its placement relative to the articular surface of the subchondral bone is appropriate. If correct, the screw holes can be drilled with assurance that the screws will not enter the articular space. If not correctly located as indicated by K-wire fluoroscopic visualization, the plate can be repositioned, the K-wire re-drilled and re-examined until placement is correct.

The second portion 104 of the jig includes longitudinally displaced holes or slots 130, 132, 134, as described in detail in U.S. Pat. No. 6,926,720, to longitudinally align drill guides with the screw holes 34, 36, 38 of the intracellular portion 14 of the fixation device 10. In accord with yet another aspect of the invention, the second portion 104 also includes a K-wire guide hole 136 configured to direct a K-wire 138 at a fixed angle into the K-wire alignment hole 142 of the nail portion of the fixation device. Similar to above, prior to drilling any holes into the diaphysis for the screws for the nail portion, a K-wire is drilled through the K-wire guide hole in the second portion and its placement can be viewed under fluoroscopy to ensure its placement relative to the diaphysis is appropriate. If correct, the screw holes can be drilled with assurance that the screws will be properly aligned relative to the axis of the diaphysis. If not correctly aligned as indicated by fluoroscopic visualization, the nail portion can be repositioned, the K-wire re-drilled and re-examined until placement is correct.

The jig is usable in combination with drill guides, bits and gauges as described in previously incorporated U.S. Pat. No. 6,926,720.

There have been described and illustrated herein embodiments of a fixation device and implantation jig therefor. While particular embodiments of the invention have been described, it is not intended that the invention be limited thereto, as it is intended that the invention be as broad in scope as the art will allow and that the specification be read likewise. For example, while pegs have been described for use within the fixation device, other fixed angle bone fixators can be used as well. It will therefore be appreciated by those skilled in the art that modifications could be made to the provided invention without deviating from its spirit and scope as claimed.

What is claimed is:

1. An implantation jig for use with a fracture fixation device having a metaphyseal plate portion provided with first screw holes for receiving bone fasteners and an intramedullary nail portion having a portion with second screw holes, comprising:
  a) a first portion having front and rear portions, and a lower surface for placement on the plate portion of the fixation device over the first screw holes, said lower surface including structure for referencing the jig relative to the fracture fixation device, and provided with a plurality of access openings through which holes may be drilled, the rear portion extending upward relative to the lower surface and the front portion including a first K-wire guide hole having an upper opening, a lower opening, and a first axis extending centrally through said upper and lower openings of said first K-wire guide hole, said first K-wire guide hole adapted to guide a K-wire at a first fixed angle along said first axis and a second K-wire guide hole having an upper opening, a lower opening, and a second axis extending centrally through said upper and lower openings of said second K-wire guide hole, said second K-wire guide hole adapted to guide a K-wire at a second fixed angle along said second axis, said first and second axes being oriented at opposite angles relative to each other such that said first and second axes extend at an oblique angle relative to each other below said lower surface of said first portion; and
  b) a second portion for extension over at least the portion of the nail portion including the second screw holes, said second portion provided with a plurality of parallel longitudinally displaced openings to receive a drill guide, and a third K-wire guide hole having a third axis oriented parallel to the displaced openings, said second portion being vertically displaced relative to said first portion,
  wherein a longitudinal axis extends along said first portion parallel to said longitudinally displaced openings in said second portion, the first and second guide holes are located on opposite sides of said longitudinal axis, the third guide hole extends transversely relative to said longitudinal axis, and said first and second axes of said first and second guide holes in said first portion are obliquely oriented relative to said longitudinal axis.

2. An implantation jig according to claim 1, wherein: said first and second guide holes are located at lateralmost portions of said first portion of said jig to guide K-wires alongside, but not through, a fixation device coupled beneath said first portion.

3. An implantation jig according to claim 1, wherein: the implantation jig extends away from the fixation device at a rear portion of the device contacting surface.

4. An implantation jig according to claim 3, wherein: the implantation jig extends away in a curving portion.

5. An implantation jig according to claim 1, wherein: said first and second axes of said first and second guide holes in said first portion are oriented transverse to said parallel longitudinally displaced openings in said second portion.

6. An implantation jig for use with a fracture fixation device having a fixed angle hole for a fastener, the implantation jig including a device contacting surface at which it is removably couplable to the fixation device, the improvement comprising:
  the implantation jig including a first portion having a lower surface for placement directly on the fixation device and an opposite upper surface, a first K-wire guide hole having an upper opening and a lower opening, and a second K-wire guide hole having an upper opening and a lower opening, said implantation jig defines a longitudinal axis in said first portion,
  said first K-wire guide hole having a first axis extending through a center of each of said upper and lower openings of said first K-wire guide hole, and first K-wire guide hole sized to closely receive a K-wire such that the K-wire is guided at substantially a fixed angle parallel to the fixed angle hole of the fixation device, said first K-wire guide hole being spaced apart from over the fixation device such that a K-wire guided by said first K-wire guide hole is directed at a fixed angle offset from the fixation device and not through the fixation device such that the K-wire provides a visual indication proximate the fixed angle hole of a trajectory of a fixed angle fastener inserted through the fixed angle hole, and
  said second K-wire guide hole having a second axis and sized to closely receive a K-wire such that the K-wire is guided at substantially a fixed angle opposite to said first axis, said first and second axes extending at an oblique angle relative to each other below said lower surface of said first portion, said second K-wire guide hole being spaced apart from over said fixation device such that a K-wire guided by said second K-wire guide hole is directed at a fixed angle offset from the fixation device and not through the fixation device, said first and second K-wire guide holes located on opposite sides of said longitudinal axis.

7. An implantation jig according to claim 6, wherein: the first K-wire guide hole positions a K-wire within approximately 5 mm of the axis of the fixed angle hole.

8. An implantation jig according to claim 6, wherein: the jig includes a third K-wire guide hole sized to closely receive a K-wire such that a K-wire received therethrough is guided at substantially a fixed angle, the third K-wire guide hole having a third axis which is oriented normal to an endosteal surface of the fixation device.

9. An assembly of an orthopedic implant and an implantation jig, said orthopedic implant for use with a long bone having a metaphysis and a medullary canal, said assembly comprising:
  a) the orthopedic implant including a plate portion and a longitudinally extending intramedullary portion, said plate portion adapted to seat on the metaphysis of the long bone and having a bone contacting lower surface and an opposite upper surface, and said longitudinally extending intramedullary portion sized to extend within the medullary canal of the long bone, said intramedullary portion longitudinally and vertically offset relative to said plate portion, said plate portion including a fixed angle hole for receiving a bone fixator, the fixed angle hole having an upper opening, a lower opening and a first axis that extends through a center of each of said upper and lower openings, said first axis oriented at an oblique angle relative to said upper surface of said plate portion;

b) an implantation jig including a first portion having a lower surface for placement directly on the fixation device and an opposite upper surface, a first K-wire guide hole having an upper opening and a lower opening, and a second K-wire guide hole having an upper opening and a lower opening, said implantation jig defines a longitudinal axis in said first portion, said first K-wire guide hole having a first guide hole axis extending through a center of each of said upper and lower openings of said first K-wire guide hole, and first K-wire guide hole sized to closely receive a K-wire such that the K-wire is guided at substantially a fixed angle parallel to the fixed angle hole of the fixation device, said first K-wire guide hole being spaced apart from over the fixation device such that a K-wire guided by said first K-wire guide hole is directed at a fixed angle offset from the fixation device and not through the fixation device such that the K-wire provides a visual indication proximate the fixed angle hole of a trajectory of a fixed angle fastener inserted through the fixed angle hole, and said second K-wire guide hole having a second guide axis axis and sized to closely receive a K-wire such that the K-wire is guided at substantially a fixed angle opposite to said first axis, said first and second guide hole axes extending at an oblique angle relative to each other below said lower surface of said first portion, said second K-wire guide hole being spaced apart from over said fixation device such that a K-wire guided by said second K-wire guide hole is directed at a fixed angle offset from the fixation device and not through the fixation device, said first and second K-wire guide holes located on opposite sides of said longitudinal axis; and c) a screw element that couples said jig to said implant.

10. The assembly of claim 9, wherein:

said intramedullary portion includes an endosteal bone contacting surface on an opposite side of said implant relative to said lower surface of said plate portion and at least one fixed angle hole having an axis oriented normal to said endosteal surface, and a K-wire alignment hole to orient a K-wire at a fixed angle relative to said at least one fixed angle hole, said K-wire alignment hole substantially parallel to and closely spaced relative to the axis of the fixed angle hole in said nail portion, and said implantation jig including a second portion offset and parallel to said intramedullary portion, said second portion including a second K-wire guide hole oriented parallel to the second K-wire alignment hole, said second portion being vertically displaced relative to said first portion.

11. An assembly according to claim 9, wherein:

said first portion of said implantation jig includes front and rear portions, said first K-wire guide hole provided at said front portion, and said rear portion including an upward curve relative to a lower surface of said first portion.

12. An assembly according to claim 9, wherein:

said first portion of said implantation jig includes front and rear portions, and said first K-wire guide hole is provided at said front portion, and said rear portion curves upward relative to an implant contacting surface of said first portion.

13. An assembly according to claim 9, wherein:

said screw element includes a cannulated drill guide which engages the implant and applies a force against said jig.

14. An implantation jig according to claim 9, wherein:

said first axis and said second axis are no more than 5 mm apart.

* * * * *